US006548531B2

(12) United States Patent
Breimer et al.

(10) Patent No.: US 6,548,531 B2
(45) Date of Patent: Apr. 15, 2003

(54) METHOD FOR CANCER THERAPY

(75) Inventors: Lars Holger Breimer, Danbury, CT (US); Kapil Dhingra, Tenafly, NJ (US); Urvashi Hooda Dhingra, Cedar Grove, NJ (US); Steve Ritland, Paterson, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/055,451

(22) Filed: Jan. 23, 2002

(65) Prior Publication Data

US 2002/0156118 A1 Oct. 24, 2002

Related U.S. Application Data

(60) Provisional application No. 60/267,874, filed on Feb. 9, 2001.

(51) Int. Cl.$^7$ ............................................. A61R 31/405
(52) U.S. Cl. ...................................................... 514/414
(58) Field of Search ......................................... 514/414

(56) References Cited

U.S. PATENT DOCUMENTS

| | | | |
|---|---|---|---|
| 5,057,614 A | | 10/1991 | Davis et al. |
| 5,641,803 A | | 6/1997 | Carretta et al. |
| 5,670,537 A | | 9/1997 | Canetta et al. |
| 6,048,887 A | | 4/2000 | Dhingra et al. |
| 6,080,777 A | * | 6/2000 | Schiff ......................... 424/1.11 |
| 6,277,844 B1 | * | 8/2001 | Spector et al. ............... 514/215 |
| 6,335,194 B1 | * | 1/2002 | Bennett et al. .............. 424/649 |
| 6,350,786 B1 | | 2/2002 | Albano et al. |
| 2002/0052409 A1 | * | 5/2002 | Ghosh ......................... 514/523 |

OTHER PUBLICATIONS

Trivedi C. Redman B. Flaherty L. E. Kucuko Du W. Heibrun L. K. Hussain M. Weekly 1–hour Infusion of Paclitaxel. Clinical Feasibility and Efficacy in Patients with Hormone–refractory Prostate Carcinoma. Cancer vol. 89(2): pp. 431–436, 2000.
2000 (PDR) Physicians' Desk Reference, Medical Economics Co., 2000 (PDR® entry for Taxol injection (Bristol–Myers Squibb Oncology/Immunology) pp. 881–887.
Paclitaxel in Advanced Non–Small Cell Lung Cancer: An Alternative High–Dose Weekly Schedule. A Kerley, Wallace III MD, Chest. vol. 117(4) Suppl. 1, 4/00 152S–155S.
Preclinical Characterization of Ro 31–7453, A New Cell Cycle Inhibitor S. Ritland et al. Proceedings of the European Spring Oncology Conference, Apr. 2000.
Phase 1 Clinical & Pharmacokinetic Study of the Novel Cell Cycle Inhibitor Ro 31–7453, Cassidy et al. Proceedings of the American Society for Clinical Oncology, May, 2000.
Evaluation of Effects of Dose and Schedule on Efficacy and Toxicity of Orally Administered Ro 31–7453 in Tumor Bearing Nude Mice, Dhingra, U. et al., *Proceedings of the American Association for Cancer Research Annual Meeting, Apr. 1–5, 2000.*
The Effect of Ro 31–7453 on the Growth of MTLn3 Rat Mammary Adenocarcinoma Cells at Primary and Metastatic Sites, Goggin, B.S., et al., *Proceedings of the American Association for Cancer Research Annual Meeting, Apr. 1–5, 2000.*
Comparison of Effect of First and Second Course of Treatment of Orally Administered Ro 31–7453 on Efficacy and Toxicity in Two Human Xenograft Models in Nude Mice, Dhingra, U. et al., *Proceedings of the American Association for Cancer Research Annual Meeting, Apr. 1–5, 2000.*
Ro 31–7453 Inhibits VEGF–and bFGF–Induced Corneal Angiogenesis in the Mouse, Nevins, T. D., et al., *Proceedings of the American Association for Cancer Research Annual Meeting, Apr. 1–5, 2000.*
Identification and Preclinical Characterization of Metabolites of Ro 31–7453, A New Cell–Cycle Inhibitor, Dhingra, U. et al., *Proceedings of the American Association for Cancer Research Annual Meeting, Apr. 1–5, 2000.*
Computational Modeling of Drug Exposure Versus Antitumor Effects for Ro 31–7453, Ke, J. et al., *Proceedings of the American Association for Cancer Research Annual Meeting, Apr. 1–5, 2000.*
Antitumor Efficacy and Pharmacokinetic Profile of Ro 31–7453 by Continuous Infusion in Nude Mice Bearing Human Tumor Xenografts, Cao, S. et al. *Proceedings of the American Association for Cancer Research Annual Meeting, Apr. 1–5, 2000.*
Weekly Paclitaxel in the Management of Ovarian Cancer [Review] Markman, M. Seminars in Oncology vol. 27 (3 Suppl 7): 37–40, 2000.
J. Natl. Cancer Inst. vol. 81(13) pp. 988–994 (Jul. 5, 1989).
A Novel Cell Cycle Inhibitor (Ro 31–7453): A Clinical And Pharmacokinetic Study in Patients with Solid Tumors, Soignet, S. et al., *Proceedings of the American Association for Cancer Research Annual Meeting, Nov., 2000.*
A Clinical and Pharmacokinetic Study of a Novel Cell Cycle Inhibitor (Ro 31–7453) In Patients with Solid Tumors, Soignet, S., et al., *Proceedings of the American Association for Cancer Research Annual Meeting, Apr. 1–5, 2000.*
Characterization of in vitro Antiproliferative Activity of Ro 31–7453, A New Cell–Cycle Inhibitor, Dhingra, U. et al., *Proceedings of the American Association for Cancer Research Annual Meeting, Apr. 1–5, 2000.*
Ro 31–7453 has in vivo Antitumor Activity Against Human Xenograft and Syngeneic Tumor Models, Dhingra, U. et al., *Proceedings of the American Association for Cancer Research Annual Meeting, Apr. 1–5, 2000.*
Preclinical Characterization of RO 31–7453, A New Cell Cycle Inhibitor, S. Ritland et al., *Proceedings of the European Spring Oncology Conference, Apr. 2000.*

* cited by examiner

Primary Examiner—James H. Reamer
(74) Attorney, Agent, or Firm—George W. Johnston; Patricia S. Rocha-Tramaloni

(57) ABSTRACT

Disclosed is a method of treating a patient suffering from cancer. The method comprises administering to a patient over a period of up to about 15 days a first component and a second component. The first component consists of a pharmaceutical composition containing as an active ingredient a compound of formula I or a pharmaceutically acceptable salt or ester of said compound. The second component consists of an injection solution containing as an active ingredient paclitaxel. The amount of each component in the combination is such that the combination is therapeutically effective. The components are administered concomitantly or sequentially in a three week to four week treatment cycle for as long as the tumor remains under control and the patient tolerates the regimen.

35 Claims, 3 Drawing Sheets

Figure 1: Compound II and paclitaxel in combination against seven different tumor cell lines

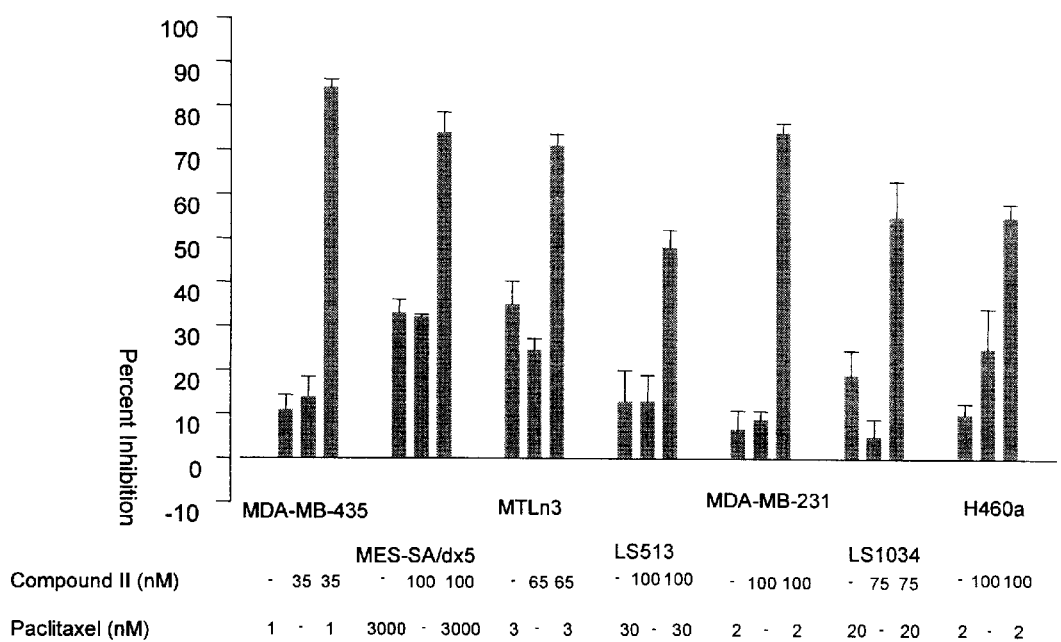

Figure 1. Compound II and paclitaxel were tested in combination against seven different tumor cell lines. Both compounds were added, at the doses shown, 24 hours after plating the cells. The growth inhibitory effect was determined by MTT assay at time points that allowed for the untreated controls to double at least four times. Results represent the mean + the standard deviation of triplicate values from a single experiment. Similar data was obtained in at least one additional experiment.

METHOD FOR CANCER THERAPY

This application claims the benefit of Provisional application Ser. No. 60/267,874, filed Feb. 9, 2001.

FIELD OF THE INVENTION

The present invention is directed to a method of cancer therapy by administering (i) a pharmaceutical composition containing a compound of formula

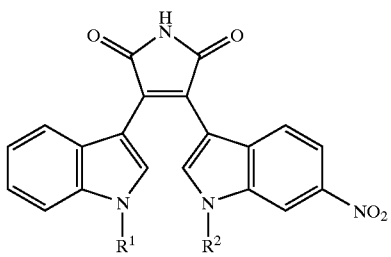

I and (ii) a pharmaceutical composition containing paclitaxel (commercially available as Taxol™). The invention is also directed to a kit containing both of the above compositions.

BACKGROUND OF THE INVENTION

The compounds of formula I below are known to be cell cycle inhibitors having potent anticancer therapeutic activity, in particular in solid tumors such as breast and colon cancers. See, e.g. U.S. Pat. Nos. 5,057,614 and 6,048,887.

Paclitaxel is also known to be useful in cancer therapeutics. See, e.g., U.S. Pat. Nos. 5,641,803 and 5,670,537 (and the references cited therein).

It has now been discovered that compounds of formula I are especially effective in cancer therapy when administered in combination with paclitaxel.

SUMMARY OF THE INVENTION

The present invention relates to a method of treating a patient suffering with cancer comprising administering to the patient, either concomitantly or sequentially, a first component consisting of a pharmaceutical composition containing as an active ingredient a compound of formula I or a pharmaceutically acceptable salt or ester of said compound and a second component consisting of a pharmaceutical composition containing paclitaxel, the amount of each component being such that the combination of components is therapeutically effective.

This combination of chemotherapeutic compounds is particularly useful in the treatment of breast, colon, rectal, lung, uterine and prostate cancers.

It was unexpectedly found that administration of the two components in accordance with the present invention results in improved antineoplastic effects that are significantly superior to the results obtained with each compound alone. Namely, administration of the two components in accordance with the present invention resulted in an improved therapeutic index (that is, superior efficacy) in comparison to either component alone without a significant increase in toxicity. Alternatively the invention permits reduction of the amount of at least one component (in comparison the amount typically given in monotherapy) while retaining a desirable therapeutic index. In preferred embodiments, the amount of both components (in comparison the amount typically given in monotherapy) is reduced affording reduced toxicity while still retaining a desirable therapeutic index.

The above findings were unexpected inasmuch as similarly designed in vitro studies using compounds of formula I in combination with other antineoplastic agents (such as gemcitabine, 5-FU and carboplatin) did not produce the magnitude of effect observed with compounds of formula I in combination with paclitaxel.

In another aspect, the invention relates to a kit. The kit comprises a first component and a second component. The first component contains one or more oral unit dosage forms of an active ingredient selected from a compound of formula I or a pharmaceutically acceptable salt or ester of said compound. The second component contains one or more injectable unit dosage forms of paclitaxel.

BRIEF DESCRIPTION OF THE FIGURES

FIG. 1 shows the enhanced antiproliferative activity of Compound II in combination with paclitaxel in a panel of cancer cell lines grown in vitro.

DETAILED OF THE INVENTION

Figure 2A:
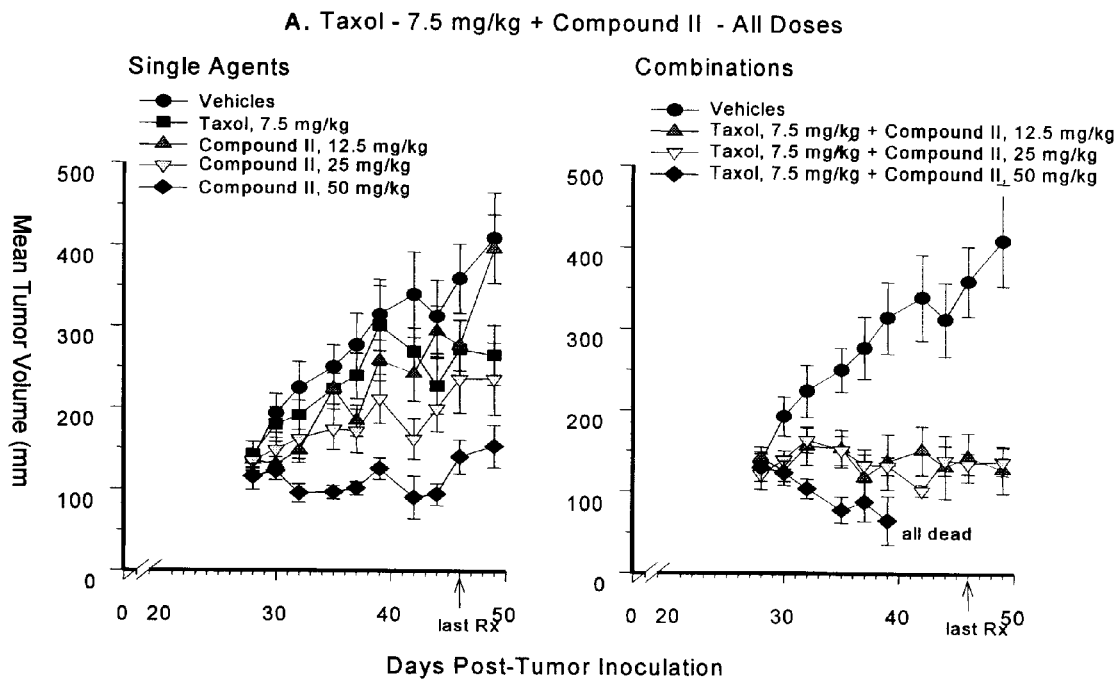
FIG. 2 shows the enhanced antitumor activity of Compound II in combination with paclitaxel against the MDA-MB-435 breast adenocarcinoma xenograft in vivo.

The term "antineoplastic" means inhibiting or preventing the development, maturation or proliferation of malignant cells.

As used herein the term "concomitant" means administration of both components during the same 24 hour period, preferably within one or two hours of each other.

The term "pharmaceutically acceptable ester" of a compound of formula I means a conventionally esterified compound of formula I having a carboxyl group, which esters retain the biological effectiveness and properties of the compound of formula I.

The term "pharmaceutically acceptable salt" of a compound of formula I as used herein is any conventional salt or base addition salt that retains the biological effectiveness and properties of the compound of formula I and which is formed from a suitable non-toxic organic or inorganic acid or organic or inorganic base. Preferred salts are cationic salts, for example, of alkali metals, especially sodium salts.

As used herein "sequential" (as in sequential adiministration) means that one component is administered more than twenty four hours after the other component, preferably within 2–15 days of the other component.

As used herein, "therapeutically effective" means an amount of drug, or combination or composition, which is effective for producing a desired therapeutic effect upon administration to a patient, for example, to stem the growth, or result in the shrinkage, of a cancerous tumor.

"Therapeutic index" is a well-recognized term of art and is an important parameter in the selection of anticancer agents for clinical trial. Therapeutic Index takes into consideration the efficacy, pharmacokinitecs, metabolism and bioavailability of anticancer agents. See, e.g., J. Natl. Cancer Inst. 81(13): 988–94 (Jul. 5, 1989).

"Tumor control" means that the perpendicular diameters of measurable lesions has not increased by 25% or more from the last measurement. See, e.g., World Health Organization ("WHO") Handbook for Reporting Results of Cancer Treatment, Geneva (1979).

The present invention is directed to a method of cancer therapy comprising the concomitant or, alternatively, sequential administration of two antineoplastic components. The first component of the present invention consists of a pharmaceutical composition containing as an active ingredient a compound of formula I, or a pharmaceutically acceptable salt or ester of said compound. The second component consists of a pharmaceutical composition containing as an active ingredient paclitaxel. The amount of each component in the combination is such that the combination is therapeutically effective to treat or ameliorate a cancerous tumor. The amount of each component administered according to the present method may, but does not have to be therapeutically effective by itself. That is, this invention specifically contemplates combinations wherein the amount of compound I and/or the amount of paclitaxel in the combination is less than a therapeutically effective amount as judged by the amounts recommended in monotherapy (i.e. a "suboptimal" amount).

In accordance with the present invention, administration of the two components, concomitantly or sequentially, synergistically enhances the treatment of cancer as compared to administering each component independently in monotherapy. The synergistic effect results in an improved therapeutic index as compared to either agent alone while toxicity remains acceptable.

Preferably, the compound of formula I is administered to the patient in an oral unit dosage form, more preferably in capsule or tablet form. The second component, paclitaxel, is administered by parenteral, preferably by intravenous administration, in association with a compound of formula I as described herein.

The first component and the second component of the present invention are administered in any amount and for any duration that is effective to maintain or decrease tumor size.

In a preferred embodiment, administration of the first component and the second component occur on the first day of a 21–28 day cycle (that is, a 3 to 4 weeks repeating cycle). The first component is administered daily for up to about 14 days, preferably for about 7 days, and more preferably for about 4 days. In a most preferred embodiment, the second component is administered only on the first day of the 21–28 day cycle.

The course of a preferred cycle is 21 or 28 days, though cycles anywhere between about 21 to about 28 days are also effective and contemplated. When the first component is administered for about 7 to about 14 days, a 28 day treatment cycle is preferred. When the first component is administered for about 4 days, a 21 day treatment cycle is preferred. At the end of the 21–28 days of each cycle, the cycle of dosing is repeated for as long as clinically tolerated and the tumor is under control or until tumor regression. Tumor "control" is a well recognized clinical parameter, as defined above. In a preferred embodiment, the cycle of dosing is repeated for up to about eight cycles.

In an alternative preferred embodiment, the second component, paclitaxel, is administered on day 1 and day 8 of a 3 week (21 days) or 4 week (28 days) cycle, preferably a 3 week cycle.

In another preferred embodiment, the second component, paclitaxel, is administered on day 1, 8 and 15 of a 3 week or 4 week cycle.

The dose intensity of compound of formula I is from about 267 $mg/m^2$/week to about 747 $mg/m^2$/week. The total overall dosage for the compound of formula I for a period of up 14 days is from about 800 $mg/m^2$ to about 2988 $mg/m^2$. A patient's body measurement in square meters ("$m^2$"), this is a "BSA (body surface area") measurement", typically ranges from about 1.4 $m^2$ to about 2.2 $m^2$. Thus, the total amount of compound of formula I to be delivered in a treatment cycle (mg) is calculated as follows:

[Dose intensity($mg/m_2$/week)]×[BSA($m^2$)]×[number of weeks in treatment cycle]

The foregoing amount of compound of formula I is divided, preferably into equal doses (though this is not required), and administered daily, as a single dose or divided into two or more doses daily, preferably twice per day, most preferably at 12 hour intervals ("Q12" or "BID"). The length of preferred treatment cycle is from about 3 to about 4 weeks.

Preferably, the compound of formula I is administered twice daily over a period of about four days. Preferred therapeutic regiments for administration of compounds of formula I are summarized in Tables 1 and 2 below.

TABLE 1

PREFERED DOSAGE REGIMENTS OF COMPOUNDS OF FORMULA 1:3 WEEK CYCLE

|  | Dose Intensity ($mg/m^2$/week) | Range Total Dose/Cycle ($mg/m^2$) | BSA Range ($m^2$) | No. of days of Dosing | Individual Dose ($mg/m^2$ BID) |
|---|---|---|---|---|---|
| Desired | 267–747 | 800–2240 | 1.4–2.2 | 4 | 100–280 |
| Preferred | 373–587 | 1120–1760 | 1.4–2.2 | 4 | 140–220 |

TABLE 2

PREFERRED DOSAGE REGIMENTS OF COMPOUNDS OF FORMULA 1:4 WEEK CYCLE

|  | Dose Intensity ($mg/m^2$/week) | Range Total Dose/Cycle ($mg/m^2$) | BSA Range ($m^2$) | No. of days of Dosing | Individual Dose ($mg/m^2$ BID) |
|---|---|---|---|---|---|
| Desired | 267–747 | 1068–2988 | 1.4–2.2 | 14 | 38–107 |
| Preferred | 373–587 | 1492–2348 | 1.4–2.2 | 14 | 53–84 |

The dose intensity of paclitaxel is from about 45 mg/m²/week to about 83 mg/m²/week. The overall dosage of the second component, paclitaxel, is from about 135 mg/m² to about 250 mg/m², administered over a fifteen day period commencing on the first day of a 21–28 day cycle. In a preferred embodiment, the paclitaxel is given in one dose on the first day of a 21-day cycle. In a second preferred embodiment, the paclitaxel is given in two doses, one on the first day and one on the eighth day, of a 21–28 day cycle. In a third preferred embodiment, the paclitaxel is given in three doses, one dose each on days 1, 8 and 15 of a 28-day cycle. While the doses do not have to be equal, they typically are. In a most preferred embodiment, the total dose of paclitaxel is administered to the patient on the first day of a 21 day cycle by approximately a three hour infusion ("i.v.").

Preferred therapeutic regiments for administration of paclitaxel are summarized in Table 3 below.

TABLE 3A

PREFERED DOSAGE REGIMENTS OF PACLITAXEL - ONCE EVERY 3 WEEK CYCLE

|  | Dose Intensity (mg/m²/week) | Range Total Dose/Cycle (mg/m²) | BSA Range (m²) | No. of days of Dosing | Individual Dose (mg/m²) |
|---|---|---|---|---|---|
| Desired | 45–83 | 135–250 | 1.4–2.2 | 1 (q3w) | 135–250 |
| Preferred | 50–67 | 150–200 | 1.4–2.2 | 1 (q3w) | 150–200 |

TABLE 3B

PREFERED DOSAGE REGIMENTS OF PACLITAXEL: ONCE WEEKLY CYCLE

|  | Dose Intensity (mg/m²/week) | Range Total Dose/Cycle (mg/m²) | BSA Range (m²) | No. of days of Dosing | Individual Dose (mg/m²) |
|---|---|---|---|---|---|
| Desired | 45–83 | 135–250 | 1.4–2.2 | 3 (qwx3)* | 45–83 |
| Preferred | 50–67 | 150–200 | 1.4–2.2 | 3 (qwx3) | 50–67 |

*qwx3 = once per week for three weeks

The dosage levels of each of the components may be modified by the physician to be lower or higher than that stated herein depending on the needs of the patient, and the reaction of the patient to the treatment. The dosages may be administered according to any dosage schedule determined by the physician in accordance with the requirements of the patient. For example, the dosages of each of the two components may be administered in single or in divided doses over a period of several days, or alternating daily schedules.

Preferably, four day treatment schedules are repeated every twenty one days, or as soon as permitted by recovery from toxicity, for so long as the tumor is under control and the patient tolerates the regiment or tumor regression. Seven, fourteen and fifteen day treatment schedules are preferably repeated every twenty eight days. Preferably, these treatment cycles are repeated for a total of up to about eight cycles (that is a total of about twenty four or about thirty two weeks).

In a particular embodiment, the present invention relates to a method of treating a patient suffering from cancer, in particular a solid cancerous tumor, comprising administering to the patient:

a first component consisting of pharmaceutical composition containing as an active ingredient a compound of formula:

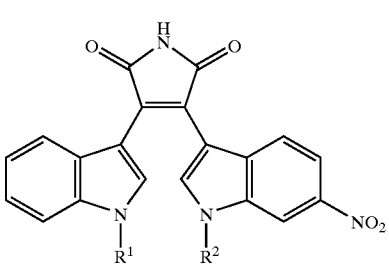

or a pharmaceutically acceptable salt or ester of said compound, wherein

R¹ is selected from the group consisting of —H, —CH₃, and —CH₂OH, and

R² is —CH₃, and wherein the active ingredient of the first component is administered daily as an oral sustained release formulation for an administration period of up to about 14 days, in a total amount of from about 800 mg/m² to about 2988 mg/m² divided over the administration period; and a second component consisting of a pharmaceutical composition containing as an active ingredient paclitaxel, wherein the paclitaxel is administered in a total amount of from about 135 mg/m² to about 250 mg/m², over about 15 days, beginning on the first day of the 21–28 day cycle;

said treatment cycle being repeated every 21–28 days for as long as the tumor remains under control and the regiment is clinically tolerated.

A preferred compound of formula I is:

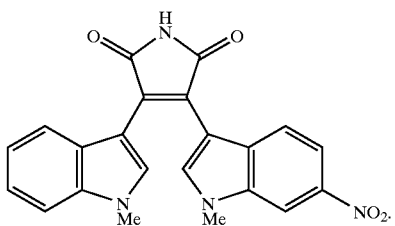

This is a known compound. See U.S. Pat. No. 5,057,614, which is incorporated herein by reference.

Other preferred compounds of formula I are

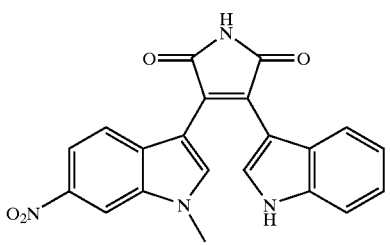

and

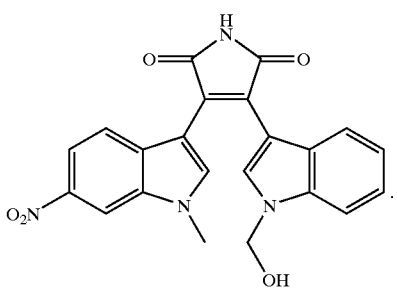

Compounds III and IV above are also known compounds. See U.S. Pat. No. 6,048,887, which is incorporated herein by reference.

The determination of tumor control ( also referred to as "maintenance") or shrinkage (also referred to as "regression") is made by known methods. For example, by evaluation of patient symptoms, physical examination, X-ray, MRI or CAT scan or other commonly accepted evaluation modalities.

In a most preferred embodiment, about 180 mg/m$^2$ of Compound II are administered twice daily (total daily dose of about 360 mg/m$^2$) for 4 consecutive days commencing on day 1 of a 21 day cycle. Also on day 1 of the cycle, preferably starting at the same time as the first dose of Compound II, 135 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is twenty four weeks).

In another most preferred embodiment, 180 mg/m$^2$ of Compound II are administered twice daily (total daily dose of 360 mg/m$^2$) for 4 consecutive days commencing on day 1 of a 21 day cycle. Also on day 1 of the cycle, preferably starting at the same time as the first dose of Compound II, about 150 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is twenty four weeks).

In another most preferred embodiment, 180 mg/m$^2$ of Compound II are administered twice daily (total daily dose of 360 mg/m$^2$) for 4 consecutive days commencing on day 1 of a 21 day cycle. Also on day 1 of the cycle, preferably starting at the same time as the first dose of Compound II, 175 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is twenty four weeks).

In another most preferred embodiment, 200 mg/m$^2$ of Compound II are administered twice daily (total daily dose of 400 mg/m$^2$) for 4 consecutive days commencing on day 1 of a 21 day cycle. Also on day 1 of the cycle, preferably starting at the same time as the first dose of Compound II, 135 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is twenty four weeks).

In another most preferred embodiment, 200 mg/m$^2$ of Compound II are administered twice daily (total daily dose of 400 mg/m$^2$) for 4 consecutive days commencing on day 1 of a 21 day cycle. Also on day 1 of the cycle, preferably starting at the same time as the first dose of Compound II, 150 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is twenty four weeks).

In another most preferred embodiment, 200 mg/m$^2$ of Compound II are administered twice daily (total daily dose of 400 mg/m$^2$) for 4 consecutive days commencing on day 1 of a 21 day cycle. Also on day 1 of the cycle, preferably starting at the same time as the first dose of Compound II, 175 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is twenty four weeks).

In another most preferred embodiment, 220 mg/m$^2$ of Compound II are administered twice daily (total daily dose of 440 mg/m$^2$) for 4 consecutive days commencing on day 1 of a 21 day cycle. Also on day 1 of the cycle, preferably starting at the same time as the first dose of Compound II, 135 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is twenty four weeks).

In another most preferred embodiment, 220 mg/m$^2$ of Compound II are administered twice daily (total daily dose of 440 mg/m$^2$) for 4 consecutive days commencing on day 1 of a 21 day cycle. Also on day 1 of the cycle, preferably starting at the same time as the first dose of Compound II, 150 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is twenty four weeks).

In another most preferred embodiment, 220 mg/m$^2$ of Compound II are administered twice daily (total daily dose of 440 mg/m$^2$) for 4 consecutive days commencing on day 1 of a 21 day cycle. Also on day 1 of the cycle, preferably starting at the same time as the first dose of Compound II, 175 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is thirty-two weeks).

In another preferred embodiment, 85 mg/m$^2$ of Compound II are administered twice daily (total daily dose of 170 mg/m$^2$) for 7 consecutive days commencing on day 1 of a 28 day cycle. Also on day 1 of the cycle, preferably starting at the same time as the first dose of Compound II, 135 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is thirty-two weeks).

In another preferred embodiment, 100 mg/m$^2$ of Compound II are administered twice daily (total daily dose of 200 mg/m$^2$) for 7 consecutive days commencing on day 1 of a 28 day cycle. Also on day 1 of the cycle, preferably starting at the same time as the first dose of Compound II, 150 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is thirty-two weeks).

In another preferred embodiment, 110 mg/m$^2$ of Compound II are administered twice daily (total daily dose of 220 mg/m$^2$) for 7 consecutive days commencing on day 1 of a 28 day cycle. Also on day 1 of the cycle, preferably starting at the same time as the first dose of Compound II, 150 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is thirty-two weeks).

In another preferred embodiment, 121 mg/m$^2$ of Compound II are administered twice daily (total daily dose of 242 mg/m$^2$) for 7 consecutive days commencing on day 1 of a 28 day cycle. Also on day 1 of the cycle, preferably starting at the same time as the first dose of Compound II, 175 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is thirty-two weeks).

In another preferred embodiment, 134 mg/m$^2$ of Compound II are administered twice daily (total daily dose of 268 mg/m$^2$) for 7 consecutive days commencing on day 1 of a 28 day cycle. Also on day 1 of the cycle, preferably starting at the same time as the first dose of Compound II, 175 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is thirty-two weeks).

In another preferred embodiment, 147 mg/m$^2$ of Compound II are administered twice daily (total daily dose of 294 mg/m$^2$) for 7 consecutive days commencing on day 1 of a 28 day cycle. Also on day 1 of the cycle, preferably starting at the same time as the first dose of Compound II, 175 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is thirty-two weeks).

In another preferred embodiment, 160 mg/m$^2$ of Compound II are administered twice daily (total daily dose of 320 mg/m$^2$) for 7 consecutive days commencing on day 1 of a 28 day cycle. Also on day 1 of the cycle, preferably starting at the same time as the first dose of Compound II, 175 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is thirty-two weeks).

In another preferred embodiment, 75 mg/m$^2$ of Compound II are administered twice daily (total daily dose of 150 mg/m$^2$) for 14 consecutive days commencing on day 1 of a 28 day cycle. Also on day 1 of the cycle, preferably starting at the same time as the first dose of Compound II, 135 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is thirty-two weeks).

In another preferred embodiment, 75 mg/m$^2$ of Compound II are administered twice daily (total daily dose of 150 mg/m$^2$) for 14 consecutive days commencing on day 1 of a 28 day cycle. Also on day 1 of the cycle, preferably starting at the same time as the first dose of Compound II, 150 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is thirty-two weeks).

In another preferred embodiment, 75 mg/m$^2$ of Compound II are administered twice daily (total daily dose of 150 mg/m$^2$) for 14 consecutive days commencing on day 1 of a 28 day cycle. Also on day 1 of the cycle, preferably starting at the same time as the first dose of Compound II, 175 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is thirty-two weeks).

In another preferred embodiment, 100 mg/m$^2$ of Compound II are administered twice daily (total daily dose of 200 mg/m$^2$) for 14 consecutive days commencing on day 1 of a 28 day cycle. Also on day 1 of the cycle, preferably starting at the same time as the first dose of Compound II, 135 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is thirty-two weeks).

In another preferred embodiment, 100 mg/m$^2$ of Compound II are administered twice daily (total daily dose of 200 mg/m$^2$) for 14 consecutive days commencing on day 1 of a 28 day cycle. Also on day 1 of the cycle, preferably starting at the same time as the first dose of Compound II, 150 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is thirty-two weeks).

In another preferred embodiment, 100 mg/m$^2$ of Compound II are administered twice daily (total daily dose of 200 mg/m$^2$) for 14 consecutive days commencing on day 1 of a 28 day cycle. Also on day 1 of the cycle, preferably starting at the same time as the first dose of Compound II, 175 mg/m$^2$ of paclitaxel are administered as a 3 hour i.v. infusion. This treatment is repeated every twenty one days, or as soon as permitted by recovery from toxicity, for so long as the tumor is under control and the patient tolerates the regiment or tumor regression. Preferably, the cycles are repeated for a total of up to eight cycles (that is thirty-two weeks).

In accordance with the present invention, a kit useful for treating cancer is also provided. The kit comprises a first component and a second component. The first component contains one or more oral unit dosage forms, preferably capsules, of an active ingredient, each unit containing from about 50 mg to about 200 mg of the active ingredient, wherein the active ingredient is a compound of formula I. The second component contains a vial containing one or more unit dosage forms of paclitaxel as an active ingredient, each unit containing about 30 mg to about 400 mg.

Preferably, the first component contains a sufficient number of units so that a patient can administer up to about 2 grams per day of the active ingredient for a period of about four to 14 days and the second component contains a sufficient number of doses so that a patient can administer up to 400 mg per day for a period of about 3 days.

In another aspect of this invention, the two components herein described above are administered together with radiotherapy or alternatively together with another anticancer agent.

The present invention may be exemplified by the Examples below, which illustrate the invention without limitation.

EXAMPLES

Example 1

In Vitro Assay

Description of Tumor Cell Lines and Cultures

Cell lines used for the in vitro studies were as follows: LS1034 and LS513 (both human colon carcinoma cell lines), MDA-MB-231 and MDA-MB-435 (both human mammary adenocarcinoma cell lines), MTLn3 (rat mammary adenocarcinoma cell line), H460a (human lung carcinoma), MES-SA/Dx5 (human uterine carcinoma cell line).

Cell lines were maintained in the designated medium (RPMI 1640 for LS1034, LS513 MDA-MB-435, MTLn3, and H460a; Dulbecco's modified medium for MDA-MB-231; McCoy's 5A medium for MES-SA/Dx5) supplemented with 10% heat-inactivated Fetal Bovine Serum (HI-FBS; Gibco/BRL, Gaithersburg, MD), 2–4 mM L-glutamine (Gibco/BRL), 50–100 units/ml penicillin and 50–100 µg/ml streptomycin (Gibco/BRL) with the following modifications.

H460a cells were grown in 20% HI-FBS (Gibco/BRL), and were grown in the absence of antibiotics. MES-SA/Dx5 cells were continuously maintained in 52 µg/ml doxorubicin (Sigma). Unless otherwise indicated, all media are from GIBCO/BRL (Gaithersburg, Md.).

The H460a cell line was a generous gift from Dr. Jack Roth from the M.D. Anderson Cancer Center at the University of Texas. MDA-MB-435 cells were given to us by Dr. Patricia Steeg from the National Cancer Institute upon permission of Dr. Janet Price of M.D. Anderson Cancer Center, University of Texas. MTLn3 cells were obtained from Anthony Neri, Department of Oncology, Hoffmann-La Roche Inc., Nutley, N.J. All other cell lines were obtained from the American Tissue Culture Collection (ATCC), Manassas, Va.

Tissue Culture Experiment and MTT Assay. Cells were harvested in log-phase growth, suspended in tissue culture media, and 180 µl of cell suspension containing 2×10$^3$ cells was added to the individual wells on a 96-well microtitre plate. Plates were incubated overnight at 37° C. in a humidified atmosphere of 5% CO$_2$ before adding compounds. Paclitaxel (NaPro Biotherapeutics) and Compound II stock solutions were prepared in DMSO and diluted in complete media before adding to the appropriate wells in a volume of 10 µl. The final concentration of DMSO did not exceed 0.2%. Plates were incubated for an additional six days at 37° C. in a humidified atmosphere of 5% CO$_2$, at which time the antiproliferative activity of the compound combinations were assessed using the MTT assay (3-(4,5-dimethylthiazole-2-yl)-2,5-diphenyl-2H-tetrazolium bromide) according to the procedure of Denizot and Lang (Denizot, F. and Lang, R. *J Immunol. Methods* 1986, 89, 271–277). Fifty µl of 5 mg MTT(Sigma)/ml phenol red-free RPMI 1640 supplemented with 1 mM sodium pyruvate and adjusted to pH 7.2, was added to the contents of each well and the plates were incubated for an additional 3 hours. Supernatant solutions were removed by inverting and blotting the plates and 50 µl ethanol was added to each well. Plates were shaken on a Bellco micro-orbital shaker for approximately 15 minutes to dissolve the formazan crystals. The absorbance of the wells was read on a microplate spectrophotometer using 570 nm test wavelength and 660 nm reference wavelength (Bio-Tek EL320). The mean absorbance of triplicate drug-treated wells was compared to that of control wells (cells cultured without drug) and the results were expressed as percent of control using the formula: [(Experimental−Control)/ Control] ×100.

Findings: The antiproliferative activity of Compound II in combination with paclitaxel was evaluated in vitro using a tetrazolium dye assay in seven different tumor cell lines derived from a variety of cancers. FIG. 1 and Table 4 show that in cell culture studies with MDA-MB-435 (breast), H460a (lung), MES-SA/dx5 (uterine), LS513 (colon), MTLn3 (breast), LS1034 (colon), and MDA-MB-231 (breast) tumor cells, Compound II in combination with paclitaxel produced a statistically significant greater growth inhibitory effect than that produced by either compound alone at the same concentrations. The results were most dramatic in MDA-MB-435 cells, where doses that gave 10–15% growth inhibition as single agents gave greater than 80% inhibition when combined. The in vitro studies demonstrate dose combinations of Compound II with paclitaxel that provide superior antiproliferative activity compared to corresponding doses of these same agents in monotherapy.

TABLE 4

Statistical comparisons for various combinations of Compound II in combination with paclitaxel in vitro

| Cell Line | Concentration Paclitaxel (nm) | Concentration Compound II (nm) | p value |
|---|---|---|---|
| MDA-MB-435 | 1.0 | 35 | <.001 |
| MESSA/dx5 | 3000 | 100 | <.001 |
| MTLn3 | 3 | 65 | <.001 |
| LS513 | 30 | 100 | .002 |
| MDA-MB-231 | 2 | 100 | <.001 |
| LS1034 | 20 | 75 | .005 |
| H460a | 2 | 100 | .01 |

Table 4: The significance of combination therapy on growth inhibition was determined by comparing the antiproliferative activity of each compound used as a single agent versus the activity of the compounds when used in combination at the same concentrations. Statistical analyses were performed using the unpaired t-test. SigmaStat for Windows (Jandel Scientific, SanRafael, CA) was used for statistical calculations.

Example 2

In Vivo Assay

Mice: Female, BALB/c nu/nu athymic nude mice at 4–6 weeks of age were obtained from Charles River Laboratories. Animals had free access to food and water and were housed in a 12-hour light/dark cycle.

Drug Preparation and Treatment: Suspensions of Compound II were prepared by combining the drug and Pluronic F68 block copolymer at 1:9 or 1:18 ratios of drug to polymer, to prepare suspensions in the concentration range 0–10 mg/ml and 20 mg/ml respectively. The mixture was heated to between 150–190° C., and the drug was solubilized in the molten polymer to obtain a clear solution. This solution (the "glass") was then cooled to form a solid dispersion. The solid dispersion for intraperitoneal formulation was hydrated with 2.5% dextrose solution (aqueous) by stirring at 4° C. overnight to obtain a fine suspension. Paclitaxel was purchased as a powder from NaPro Biotherapeutics, Inc. (CAS #33069-62-4). Paclitaxel was weighed and dissolved in EtOH with thorough mixing and sonication. Cremophor (at 37° C.) was added to the Paclitaxel/EtOH solution. Dilutions were made from this stock solution and the final excipient, 0.9% NaCl at 37° C., was added to each dose formulation just prior to dosing. The final ratio of liquid components (EtOH, Cremophor, and saline) were 5:5:90, respectively. The experiment consisted of 16 groups which contained a vehicle group, 3 groups given Paclitaxel at 7.5, 15 and 30 mg/kg as a single agent, 3 groups given Compound II at 12.5, 25 and 50 mg/kg as a single agent and 6 combination groups of all doses of Paclitaxel and Compound II. Paclitaxel vehicle (Ethanol/Cremophor/Saline) was given intra-peritoneally (i.p.), 0.5 ml, q.d., 5×/week, along with the Compound II vehicle (18% Pluronic in 2.5% dextrose solution) given i.p., 0.2 ml, twice per day (b.i.d.), 7 days/week. Compound II was administered as 0.2 ml to mice i.p., b.i.d., 7×/week, using a 1 cc syringe and a 25 gauge needle. Paclitaxel was administered to mice i.p. at 7.5 and 15 mg/kg, q.d., 5×/week while the 30 mg/kg dose was administered q.d., 3×/week. Paclitaxel was administered in 0.5 ml using a 3 cc syringe and a 26 gauge needle.

Measurements: Cells were implanted into the mammary fat pad at the right flank of mice at $1.5 \times 10^6$ cells/mouse. Tumors were allowed to establish for 28 days. Mice bearing established tumors were assigned into 16 treatment groups consisting of 10 mice per group as follows: Tumors were measured and ranked according to size and mice bearing excessively small and large tumors were removed from consideration. The remaining mice were distributed into groups with an equal number of mice of each tumor size in each group. Tumor sizes were monitored 3 times per week by caliper measurements for three weeks. Tumor diameters were measured in two orthogonal directions. Tumor volumes were calculated using the following formula:

$$\text{Tumor Volume (mm}^3) = D \times d_2/2,$$

where D is the larger diameter and d is the smaller diameter.

All mice were observed and weighed as groups, 7 times per week for three weeks. The average weight of individual mice was calculated by dividing the group weight by the number of animals per group. Percent body weight change was calculated using the formula:

(Current Average Weight−Initial Average Weight/Initial Average Weight) ×100.

Statistical Analysis: Measurement of statistical significance of mean tumor volumes between treatment groups was performed using a Wilcoxon Rank Sum Test (p<0.05).

Figure 2B:
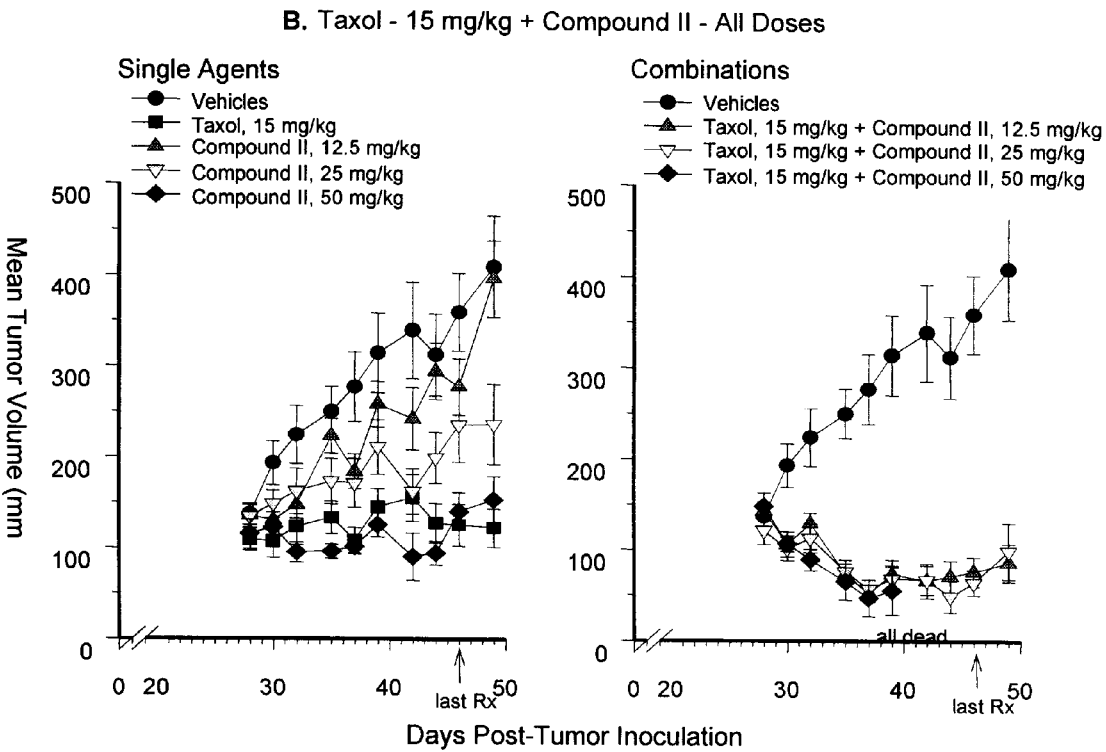
Figure 2C:
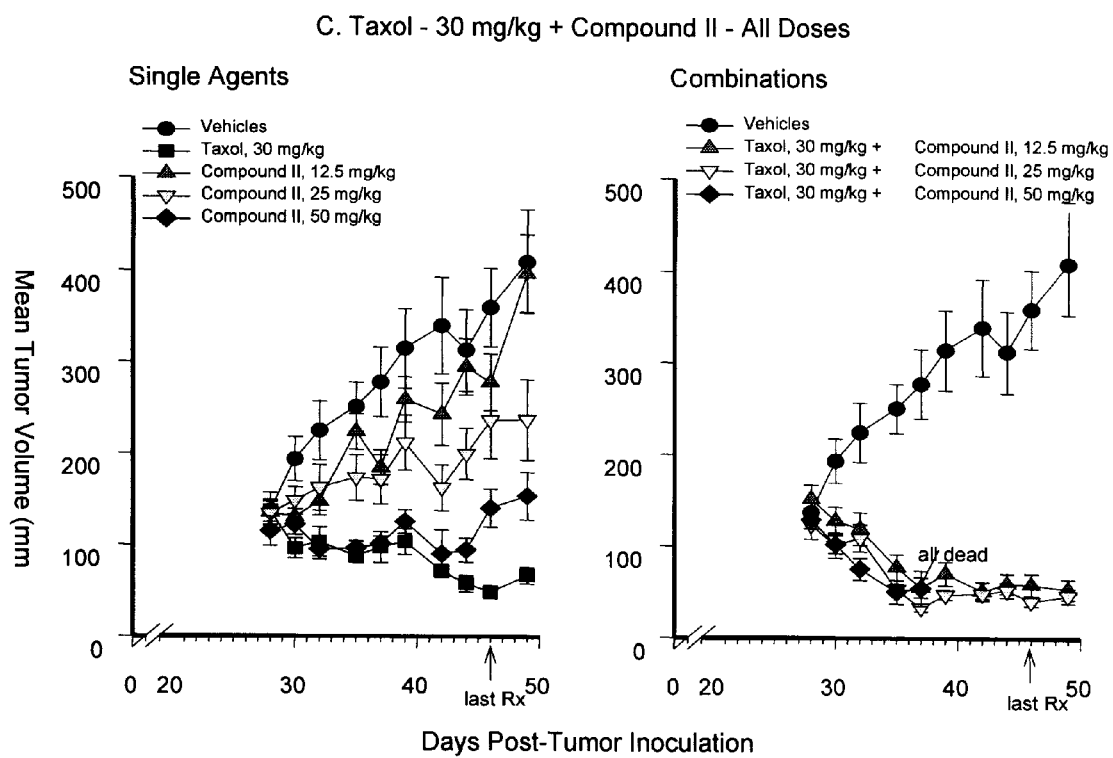

Findings: FIG. 2 and Table 5 show that significant efficacy (ranging from stasis to regression) was produced by combining low doses of Compound II and paclitaxel which were only minimally effective (e.g. slight tumor growth inhibition) as single agents. This particular combination was well tolerated, showing little evidence of enhanced toxicity. The in vivo studies demonstrate dose combinations of Compound II with paclitaxel that provide superior therapeutic index compared to corresponding regimens using these same agents in monotherapy.

TABLE 5

TOXICITY OF COMPOUND II AND PACLITAXEL, ALONE AND IN COMBINATION[a]

| Compound II Dose as mg/kg | Paclitaxel Dose as mg/kg | Max % Weight[b] Loss During Treatment | % Weight[c] Change at End of Treatment | Deaths/ Total |
|---|---|---|---|---|
| 0 | 0 | NWL[d] | +9.5 | 0/10 |
| 0 | 7.5 | NWL | +1.0 | 2/10 |
| 0 | 15 | NWL | +5.8 | 0/10 |
| 0 | 30 | NWL | +4.9 | 0/10 |
| 12.5 | 0 | NWL | +10.0 | 0/10 |
| 25 | 0 | −4.7 | +4.0 | 0/10 |
| 50 | 0 | −5.7 | +7.0 | 3/10 |
| 12.5 | 7.5 | −1.7 | +2.1 | 0/10 |
| 25 | 7.5 | −3.4 | +6.2 | 2/10 |
| 50 | 7.5 | −14.4 | NA[e] | 10/10 |
| 12.5 | 15 | −14.6 | +3.9 | 3/10 |
| 25 | 15 | −11.4 | +3.3 | 1/10 |
| 50 | 15 | −17.7 | NA | 10/10 |
| 12.5 | 30 | −10.4 | −0.4 | 1/10 |

TABLE 5-continued

TOXICITY OF COMPOUND II AND PACLITAXEL, ALONE AND IN COMBINATION[a]

| Compound II Dose as mg/kg | Paclitaxel Dose as mg/kg | Max % Weight[b] Loss During Treatment | % Weight[c] Change at End of Treatment | Deaths/ Total |
|---|---|---|---|---|
| 25 | 30 | −9.5 | +2.8 | 2/10 |
| 50 | 30 | 18.8 | NA | 10/10 |

[a]Mice bearing established tumors growing in the mammary fat pad were treated with the doses shown of either single agent or combination of agents for 3 weeks as described in the text.
[b]Weight loss at any time during treatment is expressed as a percentage (per animal) of the weight at treatment initiation. The negative sign is used to indicate that each value represents weight loss.
[c]The weight of animals at the end of the 3-week treatment period is expressed as a percentage (per animal) of the weight at treatment initiation. Positive numbers indicate weight gain, while negative numbers indicate weight loss.
[d]NWL, no weight loss.
[e]NA, not applicable (i.e., all animals had died before the end of the treatment period).
Note: During preparation of this application, it was noted that some of the mice in the above-described experiment may have been infected with *S. aureus* (based on pathologic analysis). As such, some animal deaths reported above may actually be attributable, at least in part, to the *S. aureus* infection and not to the combined treatment described above. It is also formally possible that the bacterial infection had other effects on the experimental outcomes.

The above in vitro and in vivo data identify dose combinations of Compound II and Paclitaxel that are efficacious with minimal toxicity, and that are statistically superior in terms of antiproliferative activity and/or efficacy to corresponding doses of each agent used in monotherapy.

In contrast to the results reported above, similar studies performed using combinations of Compound II with gemcitabine, 5-fluorouracil, or carboplatin capecitabine did not yield the same magnitude of synergistic effects. Specifically, combination effects in vitro with these agents did not produce the magnitude or significance of differential activity versus monotherapy observed with Compound II with paclitaxel.

What is claimed is:

1. A method of treating a patient suffering form cancer, comprising administering to the patient a therapeutically effective amount of a combination of a first component consisting of pharmaceutical composition containing as an active ingredient a compound of formula I

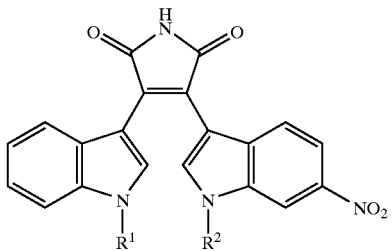

I a pharmaceutically acceptable salt or ester of said compound, wherein
  $R^1$ is selected from the group consisting of —H, —CH$_3$, and —CH$_2$OH, and
  $R^2$ is —CH$_3$;
and a second component consisting of paclitaxel.

2. The method of claim 1, wherein both components are administered concomitantly.

3. The method of claim 1, wherein both components are administered sequentially.

4. The method of claim 1 wherein the amount of compound of formula I in the combination is not by itself a therapeutically effective amount.

5. The method of claim 1 wherein the amount of paclitaxel I in the combination is not by itself a therapeutically effective amount.

6. The method of claim 1, wherein the pharmaceutical composition of the first component is an oral unit dosage form.

7. The method of claim 6, wherein the active ingredient of the first component is a compound of the formula:

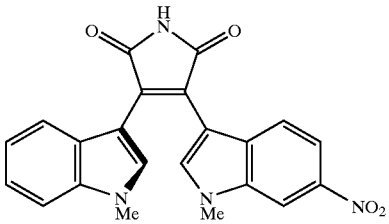

or a pharmaceutically acceptable salt or ester thereof.

8. The method of claim 6, wherein the active ingredient of the first component is a compound of the formula

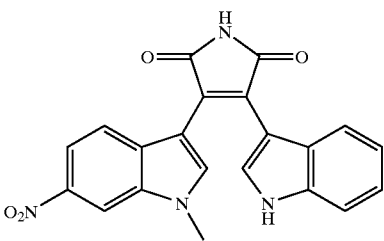

or a pharmaceutically acceptable salt or ester thereof.

9. The method of claim 6, wherein the active ingredient of the first component is a compound of the formula

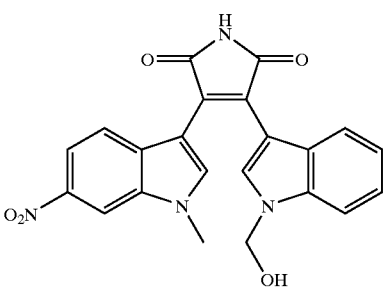

or a pharmaceutically acceptable salt or ester thereof.

10. The method of claim 1 wherein the amount of a compound of formula I is from about 800 mg/m$^2$ to about 2988 mg/m$^2$ administered over a period of up to about 14 days.

11. The method of claim 10 wherein the amount of a compound of formula I is from about 1068 mg/m$^2$ to about 2988 mg/m$^2$.

12. The method of claim 11 wherein the amount of a compound of formula I is from about 1492 mg/m$^2$ to about 2348 mg/m$^2$.

13. The method of claim 1 wherein the amount of a compound of formula I is from about 800 mg/m$^2$ to about 2240 mg/m$^2$ administered over a period of up to about 4 days.

14. The method of claim 13 wherein the amount of a compound of formula I is from about 1120 mg/m² to about 1760 mg/m².

15. The method of claim 1 wherein the dose intensity of the compound of formula I is from about 267 mg/m²/week to about 747 mg/m²/week.

16. The method of claim 15 wherein the dose intensity of the compound of formula I is from about 373 mg/m²/week to about 587 mg/m²/week.

17. The method of claim 1 wherein the active ingredient of the second component is paclitaxel.

18. The method of claim 17 wherein the amount of paclitaxel is from about 135 mg/m² to about 250 mg/m² administered over a period of up to about 8 days.

19. The method of claim 18 wherein the amount of paclitaxel is from about 150 mg/m² to about 200 mg/m² administered over a period of up to about 8 days.

20. The method of claim 19 wherein the amount of paclitaxel is about 175 mg/m² administered over a period of up to about 8 days.

21. The method of claim 17 wherein the paclitaxel is administered on day 1 of a 21-day treatment cycle.

22. The method of claim 17 wherein the dose intensity of paclitaxel is from about 45 mg/m²/week to about 83 mg/m²/week.

23. The method of claim 22 wherein the dose intensity of paclitaxel is from about 50 mg/m²/week to about 67 mg/m²/week.

24. The method of claim 19 wherein the paclitaxel is administered on days 1 and 8 of a 21–28 day treatment cycle.

25. The method of claim 19 wherein the paclitaxel is administered on days 1, 8 and 15 of a 28-day treatment cycle.

26. A method of treating a patient suffering with cancer comprising administering to the patient:
(i) a first component consisting of pharmaceutical composition containing as an active ingredient a compound of formula:

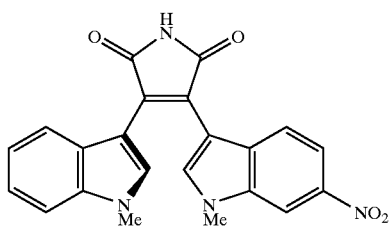

II or a pharmaceutically acceptable salt or ester of said compound,
wherein the compound of formula II is administered in an amount of from about 76 mg/m² per day to about 214 mg/m² per day for up to about 14 days starting on the first day of a 28 day cycle, and
(ii) a second component consisting of an injection solution containing as an active ingredient paclitaxel which is administered in amount of from about 135 mg/m² to about 250 mg/m² on the first day of a 28 day cycle, said 28 day cycle being repeated as long as the tumor remains under control.

27. A method of treating a patient suffering with cancer comprising administering to the patient:
(i) a first component consisting of pharmaceutical composition containing as an active ingredient a compound of formula:

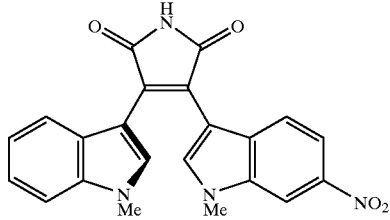

II or a pharmaceutically acceptable salt or ester of said compound, wherein the compound of formula II is administered in an amount of from about 114 mg/m² per day to about 320 mg/m² per day for up to about 7 days starting on the first day of a 28 day cycle, and (ii) a second component consisting of an injection solution containing as an active ingredient paclitaxel which is administered in amount of from about 150 mg/m² to about 200 mg/m² on the first day of a 28 day cycle, and said 28 day cycle being repeated as long as the tumor remains under control.

28. A method of treating a patient suffering with cancer comprising administering to the patient:
(i) a first component consisting of pharmaceutical composition containing as an active ingredient a compound of formula:

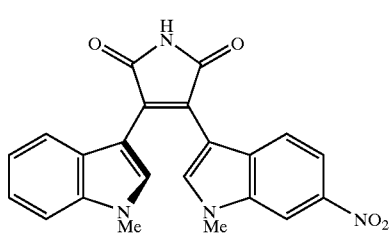

II or a pharmaceutically acceptable salt or ester of said compound, wherein the compound of formula II is administered in an amount of from about 200 mg/m² per day to about 560 mg/m² per day for up to about 4 days starting on the first day of a 21 day cycle, and (ii) a second component consisting of an injection solution containing as an active ingredient paclitaxel which is administered in amount of from about 150 mg/m² to about 200 mg/m² on the first day of a 21 day cycle, and said 21 day cycle being repeated as long as the tumor remains under control.

29. A method of treating a patient suffering with cancer comprising administering to the patient:
(i) a first component consisting of pharmaceutical composition containing as an active ingredient a compound of formula:

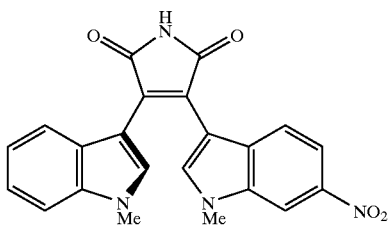

II or a pharmaceutically acceptable salt or ester of said compound, wherein the compound of formula II is administered in an amount of from about 200 mg/m² per day to about 560 mg/m² per day for up to about 4 days starting on the first day of a 21 day cycle, and (ii) a second component consisting of an injection solution containing as an active ingredient paclitaxel which is administered in amount of from about 67 mg/m² to about 125 mg/m² on the first and eighth day of a 21 day cycle, said 21 day cycle being repeated as long as the tumor remains under control.

30. A kit comprising:
(a) a first component containing one or more oral unit dosage forms of an active ingredient, each unit containing about 50 mg to about 200 mg of the active ingredient, wherein the active ingredient is a compound selected from formula I

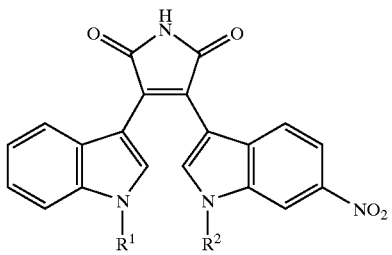

I or a pharmaceutically acceptable salt or ester said compound, wherein

R¹ is selected from the group consisting of —H, —CH₃, and —CH₂OH, and

R² is —CH₃; and (b) a second component containing a vial or series of vials, each vial containing a single injectable solution dose or multiple injectable solution doses, each dose containing as an active ingredient about 30 mg to about 400 mg of paclitaxel.

31. The kit of claim 30, wherein the first component contains a sufficient number of units so that a patient can administer about 2 grams per day of the compound of formula I or a pharmaceutically acceptable salt or ester of said compound for a period of about 4 to about 14 days and the second component contains a sufficient number of doses so that a patient can administer about 400 mg per day of paclitaxel for a period of about three days.

32. The kit of claim 31 wherein the active ingredient of the first component is

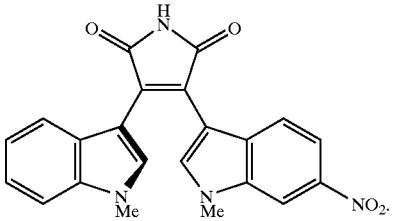

33. The kit of claim 31, wherein the active ingredient of the first component is

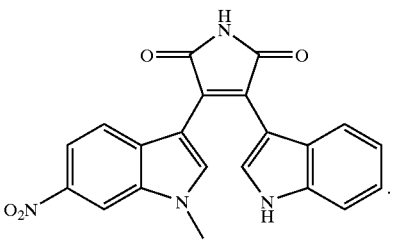

34. The kit of claim 31, wherein the active ingredient of the first component is a compound of the formula

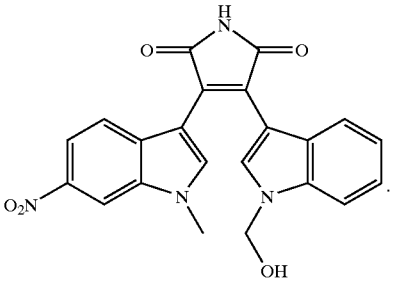

35. The method of claim 1 comprising additionally subjecting the patient to radiotherapy.

* * * * *